(12) United States Patent
Lanier, Jr. et al.

(10) Patent No.: US 7,448,991 B2
(45) Date of Patent: Nov. 11, 2008

(54) PROCESS AND SYSTEM FOR MONITORING A CONTINUOUS ELEMENT BEING INCORPORATED WITHIN A CIGARETTE FILTER

(75) Inventors: Robert C. Lanier, Jr., Moseley, VA (US); Tejinder Gill, Richmond, VA (US); Steven M. Campbell, Mechanisville, VA (US); Stephen J. Bellamah, Midlothian, VA (US)

(73) Assignee: Philip Morris USA Inc., Richmond, VA (US)

( * ) Notice: Subject to any disclaimer, the term of this patent is extended or adjusted under 35 U.S.C. 154(b) by 421 days.

(21) Appl. No.: 10/293,331

(22) Filed: Nov. 14, 2002

(65) Prior Publication Data

US 2004/0094169 A1 May 20, 2004

(51) Int. Cl.
*B31C 13/00* (2006.01)

(52) U.S. Cl. ............... 493/40; 493/12; 493/15

(58) Field of Classification Search ............ 493/40, 493/12, 15, 16, 19
See application file for complete search history.

(56) References Cited

U.S. PATENT DOCUMENTS

| | | | |
|---|---|---|---|
| 3,546,325 A | 12/1970 | Muller | |
| 4,021,217 A | 5/1977 | Bondybey et al. | |
| 4,085,928 A * | 4/1978 | Sussman | 493/14 |
| 4,091,368 A | 5/1978 | Schwartz | |
| 4,223,994 A * | 9/1980 | Stanton et al. | 355/28 |
| 4,281,671 A * | 8/1981 | Bynre et al. | 131/335 |
| 4,436,427 A | 3/1984 | Schwartz | |
| 4,549,875 A | 10/1985 | Pryor | |
| 4,639,130 A | 1/1987 | Koike et al. | |
| 4,691,647 A | 9/1987 | von Stein | |
| 4,778,271 A | 10/1988 | Kuwabara et al. | |
| 5,172,421 A | 12/1992 | Nakamura et al. | |
| 5,495,113 A | 2/1996 | Badiali et al. | |
| 5,568,715 A * | 10/1996 | Ebel et al. | 53/54 |
| 5,782,731 A * | 7/1998 | Kohn et al. | 493/16 |
| 5,970,682 A * | 10/1999 | Focke et al. | 53/53 |
| 6,761,174 B2 | 7/2004 | Jupe et al. | |
| 6,903,555 B2 | 6/2005 | Gill et al. | |
| 7,074,170 B2 | 7/2006 | Lanier, Jr. et al. | |

OTHER PUBLICATIONS

International Preliminary Examination Report dated Apr. 3, 2008 for PCT/US03/35913.

* cited by examiner

*Primary Examiner*—Sameh H. Tawfik
(74) *Attorney, Agent, or Firm*—Buchanan Ingersoll & Rooney PC

(57) ABSTRACT

A system and process for monitoring a continuous element being incorporated within a cigarette filter includes a light source and a photoresponsive device facing each other and on opposite sides of a measuring gap, and passing the continuous element through the measuring gap and detecting movement of the continuous element by the effect of the movement on at least one light beam present between the light source and the photoresponsive device. Individual lengths of the continuous cigarette filter rod being produced can be selectively rejected based on a determination of whether the continuous element has a break or a knot along its length.

26 Claims, 4 Drawing Sheets

PROCESS AND SYSTEM FOR MONITORING A CONTINUOUS ELEMENT BEING INCORPORATED WITHIN A CIGARETTE FILTER

FIELD OF THE INVENTION

The present invention relates to a system and quality control method used when incorporating a continuous element having a smoke modifying agent within a cigarette filter.

BACKGROUND OF THE INVENTION

As disclosed in U.S. Pat. No. 4,281,671, to Bynre et al., which is incorporated herein in its entirety by reference, methods are known for the continuous production of tobacco smoke filters wherein a smoke modifying agent is incorporated in the filter product by continuously entraining with the advancing supply of tobacco smoke filtering material a continuous thread or tape carrying the smoke modifying agent. The thread or tape is continuously entrained with the advancing supply of tobacco smoke filtering material before the smoke filtering material is condensed to rod form, whereby the thread or tape becomes incorporated in or on the body of the filter rod and extends continuously longitudinally thereof. The thread or tape employed according to the disclosure in the '671 patent may be of any form of nontoxic material provided that it takes up the smoke modifying agent and releases it subsequently during use of the filter. The thread or tape is preferably a textile material, such as a sewing thread or yarn. The smoke modifying agent incorporated into the thread or tape imparts an additional taste or aroma to the smoke passing through the filter in use. The smoke modifying agent is preferably applied to the thread immediately before it is incorporated in the advancing filtering material.

In the method described in the '671 patent, continuously advancing tow material such as a bonded cellulose acetate filamentary tow, is banded, sprayed with a liquid plasticizer such as triacetin, and then passed through a conventional wrapping garniture in which it is gathered to rod form and enwrapped in a paper wrapper which is secured around the formed rod by an overlapped seam. The wrapped filter rod emerging continuously from the garniture is then severed into individual lengths. At least one thread carrying a controlled amount of smoke modifying agent, applied for example by passage through a solution of the agent, is preferably continuously incorporated into the tow to move in unison therewith after the application to the tow of the liquid plasticizer.

The thread or other continuous element carrying a smoke modifying agent is led into entrainment with the tow via a mandrel, and is preferably positioned near the center and along the entire length of each filter that is cut from the continuous filter rod. The '671 patent recognizes that the thread can be monitored for breaks, for example by using a photoelectric cell device, but no details for how this would be done are provided. Furthermore, although knots are generally formed in the thread when one length of thread is joined to a subsequent length of thread, no mention is made of a process for avoiding the use of a filter rod section having a length of the thread with one or more knots formed therein.

SUMMARY OF THE INVENTION

There is a need for a system and process to monitor a thread or other continuous element carrying a smoke modifying agent as the continuous element is incorporated within a cigarette filter. An embodiment of the present invention provides a system and process for monitoring the continuous element as it is incorporated within a cigarette filter and controlling the acceptance or rejection of any portion of the continuous cigarette filter rod dependent upon the condition of the continuous element incorporated within the portion.

The system for monitoring a continuous element being incorporated within a cigarette filter according to an embodiment of the invention includes a light source and a photoresponsive device facing and on opposite sides of a measuring gap. The light source and the photoresponsive device comprise an array of light emitting and corresponding light receiving parts arranged facing and on opposite sides of the measuring gap such that multiple beams of light are formed across the measuring gap. The light emitting and light receiving parts can be fiber optics, with the array of light emitting parts and the array of light receiving parts each being formed by a fiber optic head having a plurality of holes connected with a plurality of optical fibers. An amplifier can also be connected with the fiber optics, with the amplifier having the capability of being programmed to recognize the presence or absence of the continuous element passing through the measuring gap, and the presence of anomalies such as knots in the continuous element. The amplifier can include one or more analog and/or digital channels, with a digital channel being especially useful in the recognition of anomalies such as knots, since the digital channel can transmit a signal to a Programmable Logic Controller (PLC) for control of the processing machinery at extremely high speeds. A sensing beam transmitted between the fiber optic heads may consist of one or more beams of visible red light with a wavelength of approximately 680 nm, although other wavelengths of light fall within the scope of the invention.

A method according to an embodiment of the invention includes passing the continuous element through the measuring gap, and detecting movement of the continuous element by the effect of the movement on at least one light beam present between the light source and the photoresponsive device. The intensity of a beam of light being transmitted from the multiple light emitting fiber optics to the corresponding multiple light receiving fiber optics is changed as the continuous element is moved within the measuring gap. This change in intensity causes a change in the sensor signal. The signal from the sensor is conveyed to a Programmable Logic Controller (PLC). Portions of the continuous cigarette filter rod that have received therein the monitored continuous element can then be accepted or rejected based on the detected movement of the continuous element as it is being incorporated into the cigarette filter rod.

A process for producing a tobacco smoke filter according to an embodiment of the invention includes continuously advancing a supply of tobacco smoke filtering material, continuously entraining a continuous element with the advancing supply of tobacco smoke filtering material, monitoring the continuous element by passing the continuous element through a measuring gap between a light source and a photoresponsive device and detecting movement of the continuous element by the effect of the movement on at least one light beam present between the light source and the photoresponsive device. The advancing supply of tobacco smoke filtering material is continuously condensed to a rod form, and the resulting rod is continuously severed into individual lengths, with selected ones of the individual lengths being accepted or rejected based on the detected movement of the continuous element.

A system according to an embodiment of the invention for monitoring the condition of a continuous element being incorporated within a cigarette filter rod includes an array of light emitting parts, an array of light responsive parts, the arrays being mounted in a bracket such that they are facing each other on opposite sides of a measuring gap, and a passageway defined within the bracket adapted to guide the continuous element into the measuring gap and providing a predetermined clearance around the continuous element.

BRIEF DESCRIPTION OF THE DRAWINGS

Various preferred features and advantages of the invention will become apparent upon the consideration of the following detailed description, taken in conjunction with the accompanying drawings, in which each particular reference number refers to particular parts throughout.

DESCRIPTION OF THE PREFERRED EMBODIMENTS

The present invention is directed to a system and process for monitoring a continuous element such as a string or yarn that is being incorporated into a cigarette filter rod. The filter rod is produced embedded with the yarn or other absorbent material carrying a precise amount of flavor material or other smoke-modifying agent in a precise location within the filter rod. A yarn positioning device is provided and acts as a mandrel that forms an opening in the moving filter tow and guides a yarn impregnated with flavorant into a position in the path of the moving tow. At the point where the moving yarn or other continuous element is brought into the path of the moving filter tow, the yarn is pulled by the moving tow and incorporated into a central portion of the cigarette filter. At the inlet end, the yarn positioning mandrel is open to atmosphere and provides an opening into which the yarn is introduced. The inlet end of the yarn positioning mandrel also provides an opening for the introduction of liquid flavorant, which partially fills the yarn positioning mandrel and may create a reservoir or bath of the flavorant through which the thread is passed before entering the moving tow. The yarn, being pulled by the compressed filter tow at the exit end of the positioning mandrel passes through liquid flavorant and carries the flavorant as the yarn is positioned in the filter material at the exit end of the yarn positioner.

Figure 2:
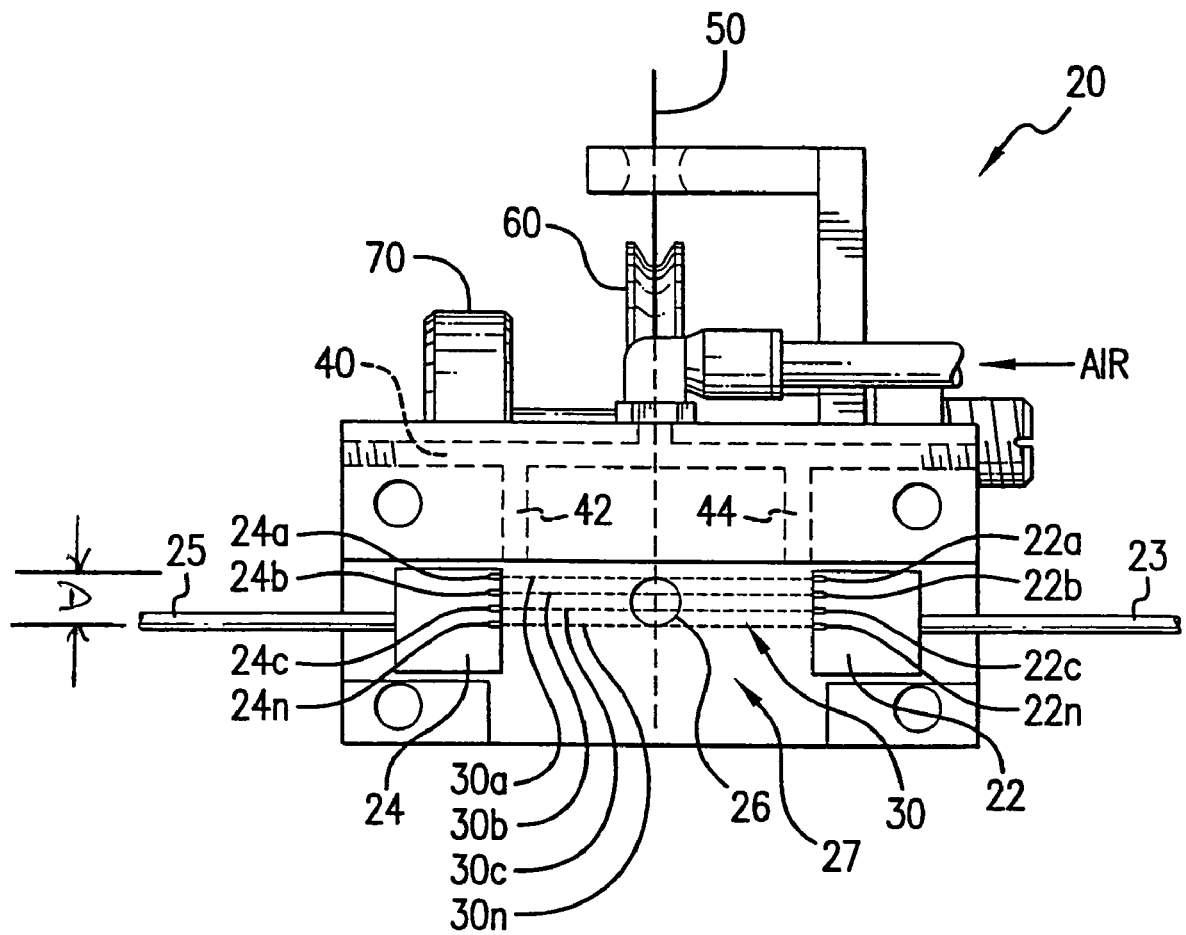
FIG. 2 illustrates an embodiment of a fixture assembly that supports the fiber optic light emitting and receiving heads in relationship to a guide element for placing the continuous element in the measuring gap between the heads.
Figure 3:
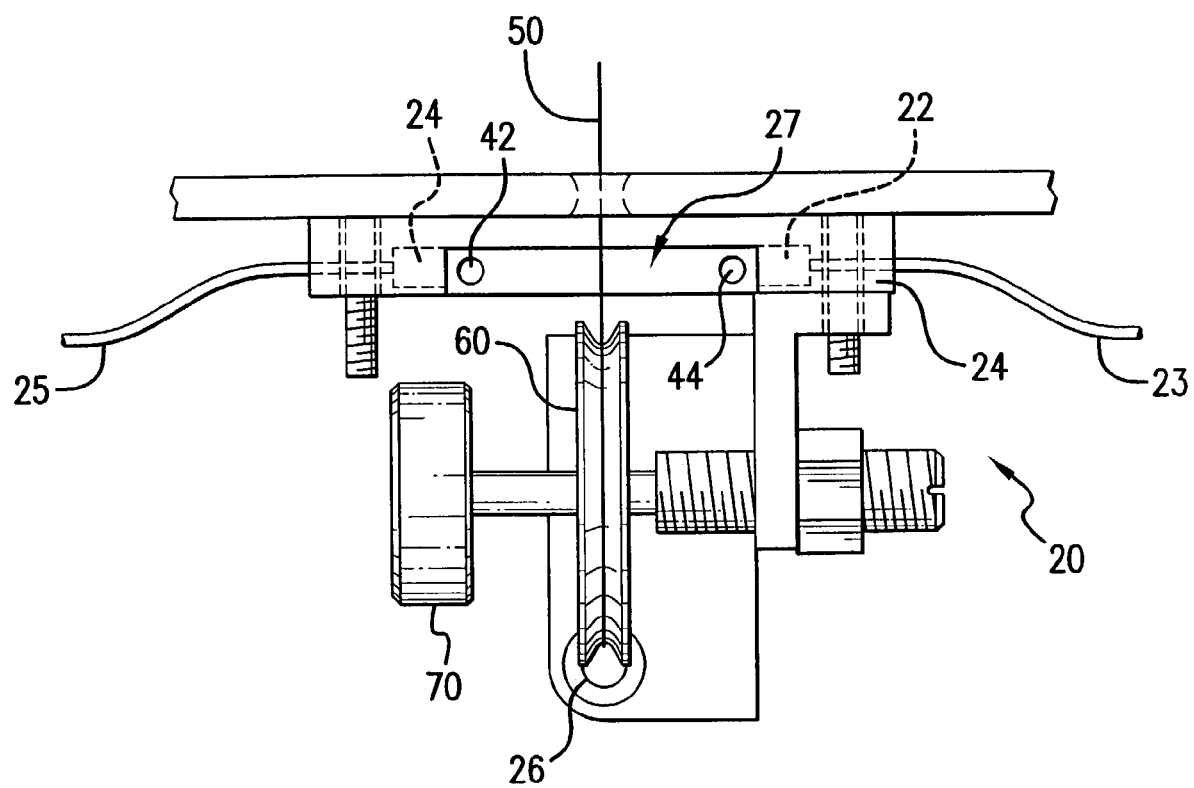
FIG. 3 illustrates another view of the fixture assembly shown in FIG. 2.
Figure 4:
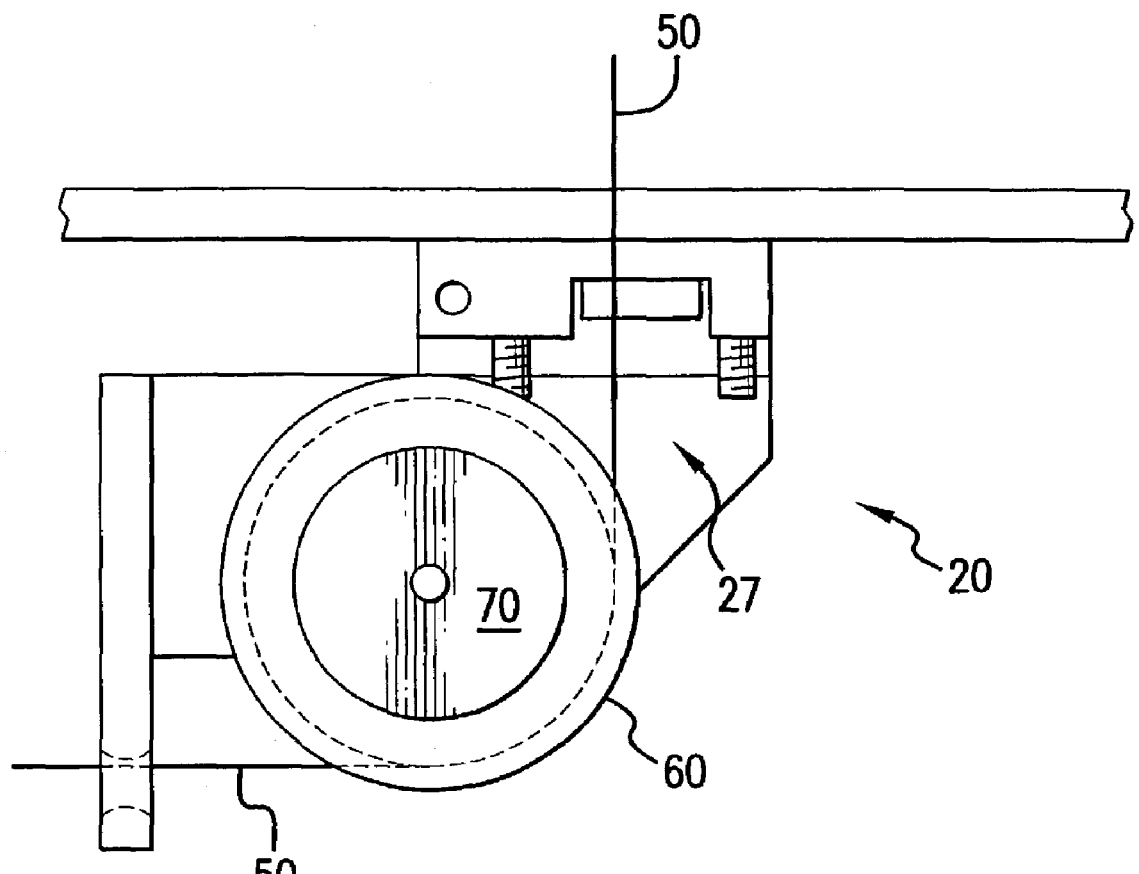
FIG. 4 illustrates yet another view of the fixture assembly shown in FIG. 2.

In the process for monitoring the yarn or other continuous element according to an embodiment of the invention, the continuous element is passed through one or more light beams before it gets to the yarn positioning mandrel on the filter making machine. Preferably an array of light emitting devices and corresponding light receiving devices are arranged facing each other and on opposite sides of a measuring gap through which the continuous element is passed before being incorporated into the cigarette filter rod. As shown in FIGS. 2-4, a bracket or fixture assembly 20 can be provided for housing and positioning a light transmitting fiber optic head 22 and a light receiving fiber optic head 24 on opposite sides of a measuring gap 27. The bracket 20 can also support a wheel or pulley 60 that guides the continuous element 50, particularly in the case of a continuous thread or yarn made from a material such as cotton or wool that may have a tendency to create lint. The continuous element 50 is guided over the wheel 60 and through an opening 26 into the measuring gap 27.

Figure 1:
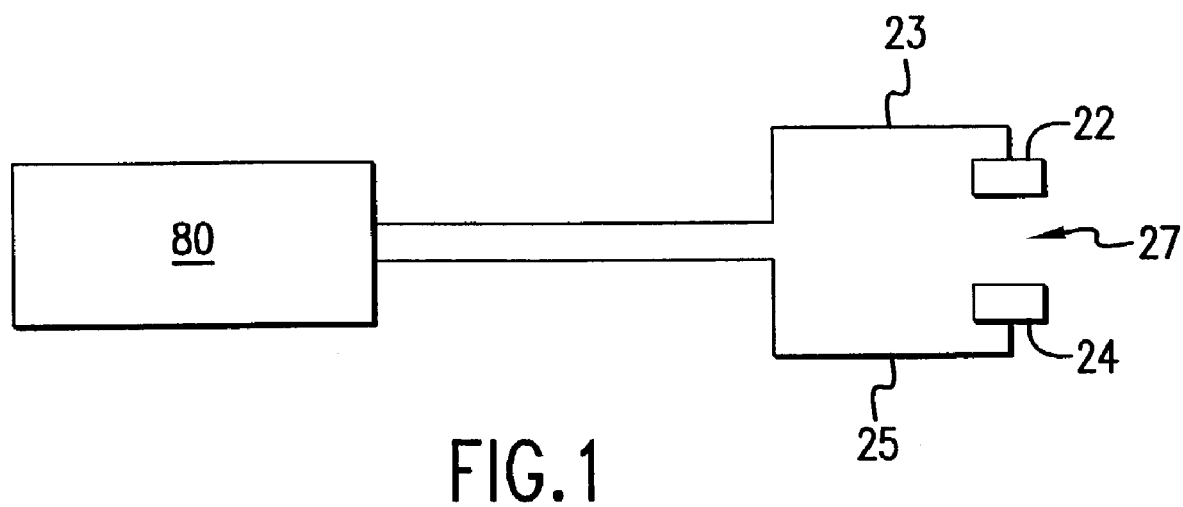
FIG. 1 illustrates a portion of a system according to an embodiment of the invention used for monitoring a continuous element to be incorporated into a cigarette filter.

As shown in FIG. 1, a photoelectric sensor includes an amplifier 80 that provides light to the light emitting fiber optic head 22 through a fiber optic 23 and receives light from light receiving fiber optic head 24 through a fiber optic 25. As an example of one possible configuration for the fiber optic heads 22 and 24, the light emitting fiber optic head 22 can have 16 holes that have attached optical fibers, and the light receiving fiber optic head 24 can have a corresponding 16 holes with attached optical fibers, the holes in the head 22 being aligned across measuring gap 27 with the holes in the head 24, and the continuous element 50 passing between the aligned holes.

A method according to an embodiment of the invention includes passing the continuous element 50 through the measuring gap 27, and detecting movement of the continuous element by a detected change in intensity of the light beam that is transmitted to the receiving end of the fiber optics. This change in intensity causes a change in the sensor signal. The amplifier 80 can have the capability of being programmed to recognize the presence or absence of the continuous element within the measuring gap 27, and the presence of an anomaly in the continuous element such as a knot. The amplifier 80 can include one or more analog and/or digital channels. The signal from the sensor can be conveyed to a programmable logic controller (PLC), which can then interpret the signal from the sensor and provide instructions to the processing machinery. In one desirable configuration, the analog channel of the amplifier 80 can be programmed to recognize the presence or absence of the continuous element, and whether the continuous element is moving properly to the point of insertion within a cigarette filter. The digital channel can be programmed to recognize anomalies such as knots in the continuous element, and provides the advantage of a very quick response and generation of a signal indicative of the presence of the anomaly.

Under normal circumstances a signal from the sensor is continuously changing as a result of movement of the continuous element 50 within the measuring gap. The variation in the intensity of the light beam produced across the measuring gap as a result of movement of the continuous element 50 through the measuring gap, can be continuously monitored and the difference in intensity over very small time periods can be continuously determined. When nothing passes in front of the fiber optics, the variation in intensity of the light beam as determined by the sensor is a relatively small value. When the continuous element 50 is passing in front of the optics, the sensor returns another value representative of the variation in intensity that is a relatively larger value. A threshold can be set in the program of the amplifier portion of the photoelectric sensor such that if the value returned by the sensor is below the threshold, indicating that the continuous element 50 is not present within the measuring gap, the machine feeding the continuous element 50 to be incorporated into a cigarette filter can be stopped.

When the continuous element 50 is moving through the gap, there is a change in the values of the intensity of the light beam as a result of the movement of the continuous element. A comparator constantly compares new and old values from the sensor. Again, a threshold value for movement of the continuous element 50 within the gap can be set such that when the continuous element 50 is present in front of the fiber optics, but is not moving because it is broken somewhere else along its path, the machine can be stopped because the difference between the sensor new and old values becomes lower than the threshold value for the movement check.

Sensor signals representative of the presence of a knot in the continuous element 50 can be detected by the digital channel and used in determining whether portions of the continuous filter rod into which the continuous element has been incorporated should be selectively discarded. A relatively large change in intensity of the light beam occurs over a relatively short period of time when an anomaly such as a knot passes between the fiber optic heads. In one desirable configuration, the digital channel is programmed to recognize such relatively large changes in intensity over a relatively short period of time, since the digital channel can provide a very rapid response to the PLC, which can in turn provide instructions to the very high speed processing equipment.

The detector for monitoring the continuous element is installed and operated on a cigarette filter making machine that runs at speeds of up to 500 meters per minute. It is therefore necessary that the photoelectric sensor operate at these high speeds and provide an output that is useful in determining whether portions of the cigarette filter rod should be discarded. In a preferred embodiment of the invention, 16 light emitting optical fibers are housed within light transmitting fiber optic block 22 that is preferably 15 mm×15 mm×5 mm, and 16 corresponding photoresponsive light receiving optical fibers are contained likewise in a second block 24 that is spaced from the first block in a first direction. The number of light emitting and light receiving parts can be varied, with the number 16 not being limiting in any way. The blocks 22, 24 can be formed with an array of holes in which individual optical fibers terminate. Bracket 20 shown in FIGS. 2-4 houses the two fiber optic blocks 22, 24 and positions the blocks on opposite sides of a measuring gap 27, into which the continuous element 50 is fed through a hole 26. The light emitting fiber optic head 22 can include an array of holes and fiber optics 22a, 22b, 22c . . . 22n, that produce light beams 30a, 30b, 30c, . . . 30n, to form a light beam 30 across the measuring gap 27. The fiber optic head 24 forms the light receiving parts with an array of holes and fiber optics 24a, 24b, 24c, . . . 24n that are aligned with the corresponding transmitting fiber optics in head 22. The light emitting parts and light receiving parts define a thread-monitoring zone having a transverse dimension D (see FIG. 2) extending in a second direction perpendicular to the first direction and perpendicular to a direction of thread travel. The thread 50 has a maximum transverse dimension in the second direction that is shorter than the transverse dimension D of the thread-monitoring zone.

The bracket 20 shown in FIGS. 2-4 can support a wheel or pulley 60 that guides the continuous element 50 into the measuring gap 27 without creating any lint since the surface of the wheel 60 in contact with the continuous element 50 moves with the continuous element rather than creating any friction. Air can also be blown through a manifold 40 and into the measuring gap 27 through openings 42, 44 to assist in keeping the measuring gap free of any lint or other debris that could interfere with the optical path or the ends of the optical fibers. The passageway 26, through which the continuous element 50 travels to enter the measuring gap 27, is sized to allow the continuous element to travel between the sending and receiving optics and to allow a knot to pass, while still being a small enough passageway to control movement of the continuous element. The number of the multiple beams of light that are broken by the continuous element passing through the measuring gap affects the intensity of the total beam of light 30 transmitted between fiber optic heads 22 and 24. The continuous cigarette filter rod being produced with the incorporated continuous element 50 is subsequently cut into individual lengths or filter plugs. A desired number of the filter plugs can be discarded if necessary before and/or after a determination that the change in intensity of light beam 30 over a given time period is not within a desired range, or exceeds a predetermined threshold, such as when a knot in the continuous element passes through the measuring gap.

The fiber optic sensor, and in particular, the amplifier 80 shown in FIG. 1, can be provided with two separate channels, an analog channel and a digital channel. Each channel has the capability of monitoring static and dynamic modes. The analog channel can check for the presence of the continuous element. In a situation where the continuous element is actually broken somewhere else along its path, but is still present within the measuring gap, the difference between the sensor's measured intensities of the light beam 30 at two sequential points in time would be less than a predetermined threshold that is met by normal movement of the continuous element within the measuring gap, and the machine can be shut down to fix the problem.

In a situation where the continuous element is moving properly through the monitoring gap on its way to being incorporated into the cigarette filter rod, the movement of the continuous element in directions transverse to the direction of travel as a result of some play within the passageway or opening 26 will result in adjacent beams of light being periodically broken by the movement of the continuous element. Hence the threshold value for the difference in intensity of the light beam at two sequential points in time will be met.

When a spool of thread or other continuous element runs out, the new spool will generally be spliced onto the existing spool. Thus, a knot will generally be created in this process. The digital channel in the photooptic sensor can be taught to look for these knots. When a knot moves through the measuring gap between the light sending and receiving optics, a relatively large change in intensity of the light beam 30 over a relatively short time period will occur as a result of the movement of the knot through the measuring gap 27. The digital channel instantaneously recognizes a knot as a result of this relatively large change in intensity and transmits the information to the PLC so that cigarette filters having received the knotted portion of the continuous element can be rejected. Some filters produced before and after the filter or filters that received a knotted portion of the continuous element can also be rejected.

In a situation where only one or a relatively small number of light beams are broken by the presence of the continuous element remaining stationary in the measuring gap, and the intensity of the light beam changes very little over a predetermined period of time, a predetermined threshold value for change in intensity of the light beam may not be reached. Accordingly, a determination is made that the string or continuous element is broken somewhere else along its path, and therefore is not moving properly through the measuring gap. The PLC can then interpret this signal from the sensor and make a determination to stop the incorporation of the continuous element into the filter rod until the location of the break is determined and the situation is repaired.

While this invention has been illustrated and described in accordance with a preferred embodiment, it is recognized that variations and changes may be made therein without departing from the invention as set forth in the claims. For example, the number of light emitting and light receiving devices that are mounted facing each other and on opposite sides of a measuring gap can be varied. The spacing between the individual light emitting devices and between the light responsive devices will determine the spacing between the light beams produced within the measuring gap. Accordingly, the determination of a change in intensity of light that indicates the presence of a knot may vary. The sensing beam itself can also vary in ways including but not limited to the wavelength of light transmitted through the fiber optics. The fiber optics and the fiber optic heads can vary and have different dimensions and configurations. The amplifier of the photoelectric sensor can be provided with just one channel, both an analog channel and a digital channel, or a plurality of analog and/or digital channels.

What is claimed is:

1. A system for monitoring a continuous thread being incorporated within a cigarette filter rod, comprising:
   a source of continuous thread;
   an array of light emitting parts operable to emit light;
   an array of light responsive parts operable to receive light from the array of light emitting parts;
   the arrays being mounted in a bracket such that they are facing each other on opposite sides of a measuring gap;
   a passageway defined within said bracket adapted to guide the thread into the measuring gap and providing a predetermined clearance around the thread;
   a positioning device comprising a mandrel that forms an opening in a moving filter tow positioned downstream from the measuring gap to entrain the thread within the cigarette filter rod, wherein the entrainment pulls the thread through the measuring gap;
   an air manifold, wherein the air manifold is capable of removing lint or debris accumulated in the passageway and/or the measuring gap;
   a photoelectric sensor connected to the light emitting parts and the light responsive parts and operable to generate signal values due to intensity of light received by the light responsive parts; and
   a programmable logic controller (PLC) which compares signal values from the photoelectric sensor and determine whether a thread present in the measuring gap is moving or stationary due to differences in the signal values output by the photoelectric sensor.

2. The system according to claim 1, wherein the array of light emitting parts are assembled in a row within a first block, and the array of the light responsive parts are assembled in a row within a second block spaced from the first block in a first direction, wherein the light emitting parts and the light responsive parts define a monitoring zone having a transverse dimension extending in a second direction perpendicular to the first direction and perpendicular to a direction of thread travel, wherein the thread has a maximum transverse dimension in the second direction that is shorter than the transverse dimension of the monitoring zone.

3. The system according to claim 2, wherein 16 light emitting parts and 16 light responsive parts are assembled within the blocks, each block having dimensions of approximately 15 mm×15 mm×5 mm.

4. The system according to claim 1, wherein the PLC is capable of determining whether a knot in the thread passes within the measuring gap.

5. The system according to claim 4, wherein said photoelectric sensor includes one or more of an analog channel and a digital channel to output signals to the PLC.

6. The system according to claim 1, wherein the PLC outputs instructions to accept or reject portions of the cigarette filter rod having received therein the thread based on changes in the photoelectric sensor signal values.

7. The system according to claim 1, further including a moving surface adapted to guide the thread into the passageway.

8. The system according to claim 7, wherein the moving surface is a grooved surface on a rotatable wheel or pulley.

9. The system according to claim 8, wherein the grooved surface comprises a groove that is aligned to guide the thread into the measuring gap.

10. The system according to claim 8, wherein the rotatable wheel or pulley includes an axis of rotation extending parallel to at least one light beam present between the light emitting parts and the light responsive parts.

11. The system according to claim 1, wherein the positioning device guides the thread into a position in a path of the moving filter tow.

12. The system according to claim 1, wherein the air manifold blows air through the passageway.

13. The system according to claim 12, further comprising openings between the air manifold and the measuring gap.

14. The system according to claim 1, wherein the source of continuous thread comprises a spool of yarn or string.

15. The system according to claim 1, wherein the programmable logic controller (PLC) recognizes absence of a thread in the measuring gap and outputs instructions to accept or reject portions of the cigarette filter rod based on changes in the photoelectric sensor signal values.

16. The system according to claim 15, wherein the PLC is connected to a machine feeding the source of continuous thread, and wherein the PLC signals the machine feeding the source of continuous thread to stop when the thread is broken.

17. The system according to claim 1, wherein the passageway surrounds the thread laterally to control lateral movement of the thread.

18. The system according to claim 1, further comprising a liquid flavorant containing reservoir or bath in the positioning device, wherein thread from the source of continuous thread passes through the liquid flavorant forming a flavored thread, wherein the positioning device is capable of incorporating the flavored thread into the cigarette filter.

19. The system according to claim 1, wherein thread from the source of continuous thread has a tautness throughout the system between the source of continuous thread, the positioning device and the cigarette filter rod formed by the system.

20. A system for monitoring a thread being incorporated within a cigarette filter, comprising:
   an array of light emitting parts;
   an array of light receiving parts opposite from the array of light emitting parts;
   a measuring gap between the array of light emitting parts and the array of light receiving parts;
   a rotatable grooved wheel or pulley with a groove aligned to feed the thread into the measuring gap, wherein the groove is sized to hold the thread within the groove;
   a passageway between the rotatable grooved wheel or pulley and the measuring gap, wherein the groove and tension on the thread guide the thread through the passageway and into the measuring gap;
   a photoelectric sensor connected to the light emitting parts and the light responsive parts and operable to generate signal values due to intensity of light received by the light responsive parts;
   a programmable logic controller (PLC) which compares signal values from the photoelectric sensor and determines whether a thread present in the measuring gap is moving or stationary due to differences in the signal values output by the photoelectric sensor; and a positioning device downstream from the measuring gap, wherein the positioning device feeds the thread into the cigarette filter and the cigarette filter pulls the thread through the measuring gap, wherein the positioning device comprises a mandrel capable of opening a moving filter tow.

21. The system according to claim 20, wherein the cigarette filter pulls the thread through the passageway into the moving filter tow, which is formed into the cigarette filter.

22. The system according to claim 20, further comprising an air manifold, wherein the air manifold is capable of removing lint or debris accumulated in the passageway and/or the measuring gap.

23. The system according to claim 20, wherein the passageway surrounds the thread and the PLC is further capable of determining whether a knot in the thread passes within the measuring gap.

24. A flavored cigarette filter manufacturing apparatus, comprising:

a continuous thread source comprising thread;

a thread monitoring device comprising:

a wheel or pulley to lead the thread through the thread monitoring device;

an array of light emitting parts and a corresponding facing array of light responsive parts, wherein the thread passes between the arrays;

a passageway through which the thread passes;

a photoelectric sensor connected to the light emitting parts and the light responsive parts and operable to generate signal values due to intensity of light received by the light responsive parts; and a programmable logic controller (PLC) which compares signal values from the photoelectric sensor and determines whether a thread present in the measuring gap is moving or stationary due to differences in the signal values output by the photoelectric sensor; and a positioning device comprising a mandrel and a flavorant containing reservoir or bath, wherein the mandrel forms an opening in a moving filter tow and guides the thread through the flavorant and into a position in a path of the moving filter tow.

25. The flavored cigarette filter manufacturing apparatus according to claim 24, wherein the thread monitoring device further comprises:

an air manifold capable of blowing air through the passageway; and the programmable logic controller (PLC), provides instructions to the cigarette manufacturing apparatus.

26. The flavored cigarette filter manufacturing apparatus according to claim 24, wherein the PLC is further capable of determining whether a knot in the thread passes within the measuring gap and outputs instructions to accept or reject portions of the cigarette filter rod based on chances in the photoelectric sensor signal values.

\* \* \* \* \*